(12) United States Patent
Durham

(10) Patent No.: US 6,245,554 B1
(45) Date of Patent: Jun. 12, 2001

(54) SEWER GAS ODOR ABATEMENT SYSTEM

(76) Inventor: James M. Durham, 1811 Bayberry Dr., Pembroke Pines, FL (US) 33024

( * ) Notice: Subject to any disclaimer, the term of this patent is extended or adjusted under 35 U.S.C. 154(b) by 0 days.

(21) Appl. No.: 09/556,656

(22) Filed: Apr. 24, 2000

Related U.S. Application Data

(60) Provisional application No. 60/132,838, filed on May 6, 1999.

(51) Int. Cl.⁷ ..................................................... A61L 9/01
(52) U.S. Cl. ...................... 435/266; 435/299.1; 210/150; 55/227; 55/233
(58) Field of Search .............................. 435/266, 297.1, 435/299.1, 299.2; 210/150; 55/220, 227, 229, 233

(56) References Cited

U.S. PATENT DOCUMENTS

| | | | |
|---|---|---|---|
| 1,972,885 | 9/1934 | Gleason et al. | 23/225 |
| 3,122,594 | 2/1964 | Kielback | 261/94 |
| 3,302,372 | 2/1967 | Hynson et al. | 55/71 |
| 3,432,994 | 3/1969 | Whiton et al. | 55/91 |
| 3,556,490 | 1/1971 | Beckman | 261/98 |
| 3,635,000 | 1/1972 | Brown | 55/89 |
| 3,793,809 | 2/1974 | Tomany et al. | 55/91 |
| 3,883,329 | 5/1975 | Dupps, Sr. | 55/222 |
| 3,907,522 | 9/1975 | Tsukamoto et al. | 55/71 |
| 3,936,281 | 2/1976 | Kurmeier | 55/71 |
| 4,110,008 | 8/1978 | Cold et al. | 55/90 |
| 4,421,534 * | 12/1983 | Walker | 55/73 |
| 4,533,367 | 8/1985 | Hadzismajlovic | 55/91 |
| 4,780,277 | 10/1988 | Tanaka et al. | 422/4 |
| 5,186,907 | 2/1993 | Yanagi et al. | 422/186.3 |
| 5,413,714 | 5/1995 | DeFilippi et al. | 210/617 |
| 5,480,538 * | 1/1996 | McCombs et al. | 210/151 |
| 5,496,778 | 3/1996 | Hoffman et al. | 437/250 |
| 5,509,946 | 4/1996 | Chu | 55/233 |
| 5,531,801 | 7/1996 | Sewell et al. | 55/223 |
| 5,634,962 | 6/1997 | Trahan et al. | 95/158 |

* cited by examiner

Primary Examiner—David A. Redding
(74) Attorney, Agent, or Firm—Head, Johnson & Kachigian

(57) ABSTRACT

A system for deodorizing malodorous sewer gas having a tower with a lower gas inlet and an upper gas outlet, malodorous gas passing into the tower through the gas inlet. Packing is positioned within the tower between the inlet and outlet. An enzyme solution recirculating system withdraws enzyme solution from the interior bottom of the tower and introduces it into an upper portion of said tower, the enzyme solution passing downward through the packing. A blower moves malodorous gas into the tower inlet and upwardly through the packing for contacting downwardly passing enzyme solution. An enzyme solution replenishment system is connected to the circulation system.

13 Claims, 3 Drawing Sheets

SEWER GAS ODOR ABATEMENT SYSTEM

This application is a conversion application related to U.S. Provisional application Ser. No. 60/132,838, filed May 6, 1999.

SUMMARY OF THE INVENTION

Any closed system for handling sewage is a potential source of odor pollution. Lift stations and pump stations where sewage is moved in a sewage treatment process are frequent sources of odor. Decomposition of sewage frequently results in production of hydrogen sulfide and other malodorous gases.

This invention provides a system and a method of treating gases that emanate from lift stations, pump stations and other similar sewage handling facilities so as to eliminate objectionable odor passing into the atmosphere.

The system herein consists essentially of passing malodorous gases generated by sewage systems upwardly through a vertical tower, the gases being contacted by a downwardly flowing enzyme solution followed by ozone neutralization. The enzyme solution is obtained by natural fermentation of food grade materials, selected strains of bacteria from which a substantially pH neutral enzyme soup is obtained that is blended with micro-nutrients and biocatalysts. The enzyme solution is cascaded downwardly through filler materials, preferably jaeger tripac ceramic skeletal spheres or PVC biochips. The filler material provides high surface areas per unit volume allowing substantial gas contact with surfaces wetted by the enzyme solution.

Enzyme solution collected in the bottom of the tower is recirculated by a pump for continuous discharge into the top of the tower. Fresh enzyme solution is continually added by means of a venturi connected to a timed solenoid valve. The venturi withdraws fresh enzyme solution from a reserve tank.

Positioned above the packing material in the upper portion of the tower is an ozone contact chamber. Ozone produced by an ozone generator is continuously conveyed into the ozone contact chamber, the noxious gases, after being contacted by the enzyme solution, are contacted by ozone within the upper portion of the tower and mixed with the noxious gases that remain before they are discharged to the atmosphere. The resultant discharge gases are substantially free of odor.

DETAILED DESCRIPTION OF THE PREFERRED EMBODIMENTS

Figure 1:
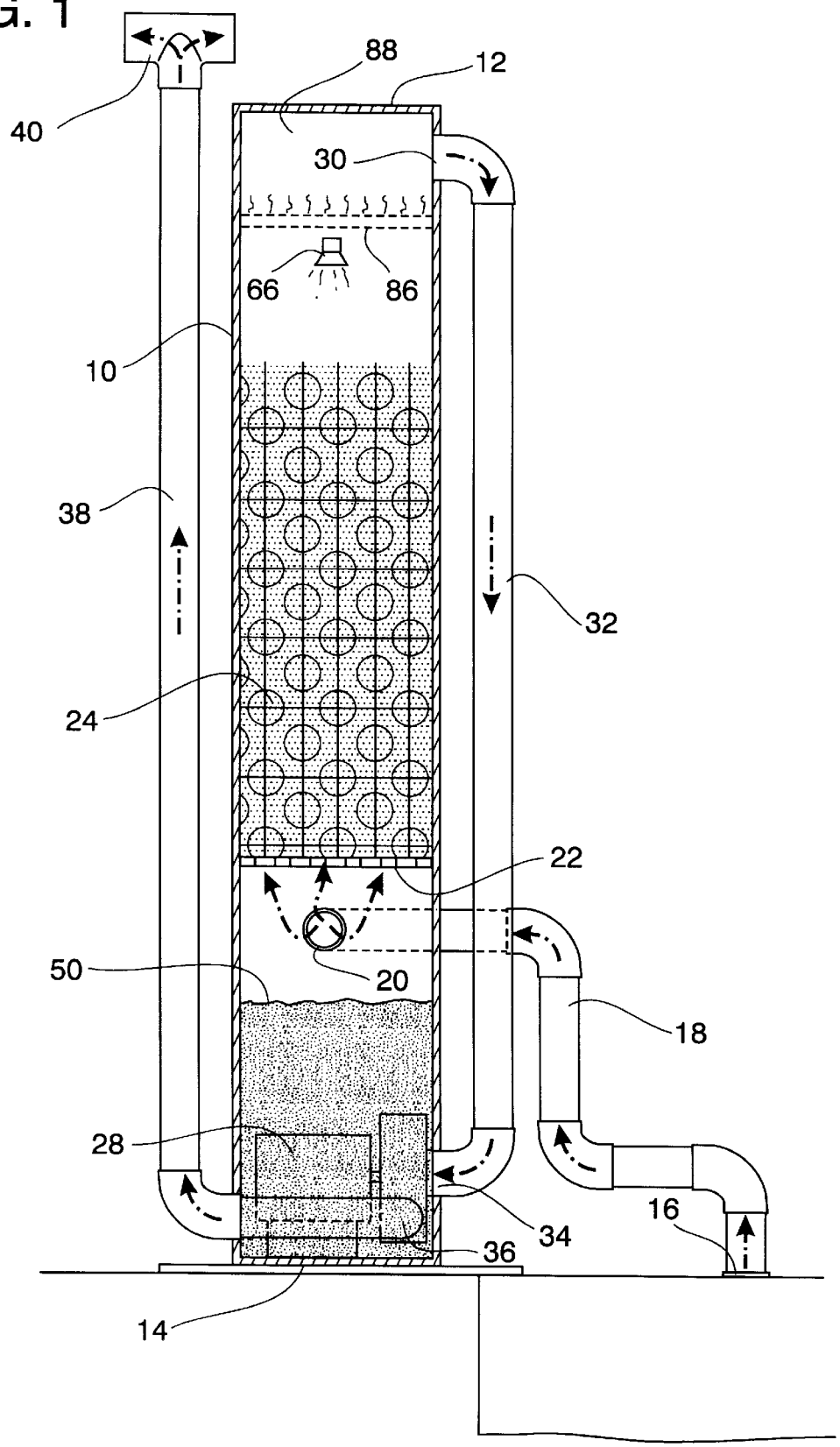
FIG. 1 is a diagrammatic elevational view of the system for practicing the method of this invention showing a tower and associated equipment by which sewer gas is contacted with an enzyme solution and ozone.

Referring to the drawing, the main element of the system is a vertical tower 10 that can be made of metal, fiberglass or plastic. Tower 10 can be made from schedule 80 PVC pipe. While the diameter and height of the tower can vary according to the volume of sewer gas being treated, for the typical lift or pump station a tower that is 12 inches in diameter and a height of about 76 inches functions satisfactorily. The tower has a closed top 12 and a closed bottom 14. The bottom can rest on a surface or on top of a typical lift or pump station that is usually formed of concrete.

The typical lift station or pump station with which the system is employed has an opening 16 from which gas can be withdrawn. The withdrawn gas flows through a conduit 18 and through an inlet opening 20 into the interior of tower 10. Within the tower and positioned above opening 20 is a horizontal perforated support plate 22. Stacked on top of support plate 22 is packing 24. The function of packing 24 is to provide a large amount of surface area in an irregular pattern past which gases can upwardly move in the tower. A commercially available type of packing that functions ideally for this application is called "Jaeger balls". This product is of spherical skeletal configuration, usually made of ceramic or other non-metallic material, and has a very high surface area to unit volume ratio. Another commercially available product, made of PVC plastic, is sold under the trademark "Bio-chips"; both of those products are designed to achieve enhanced contact between the downward passing solution and upward flowing sewer gas.

Packing 24 is stacked within the tower 10 above a perforated support plate 22 to a height that is below the tower top 12.

Sewer gas is drawn into the tower through opening 20 by means of a blower 26 operated by a motor 28. A gas outlet opening 30 in the top of the tower, immediately below top 12, has connected to it a downwardly extending tower contact pipe 32 that connects to an inlet 34 of blower 26. The outlet 36 of blower 26 connects with an exhaust pipe 38 that vertically extends upwardly to a selected height, usually above the top 12 of the tower. At the top of exhaust pipe 38 a tee fitting 40 is positioned. The tee fitting is open at both ends to permit free discharge of gases from pipe 38 to the atmosphere but to prevent rainwater from entering into the pipe.

The air flow system as described produces a path that moves air upwardly within tower 10, through packing 24 and through an upper end portion of the interior of the tower.

Figure 2:
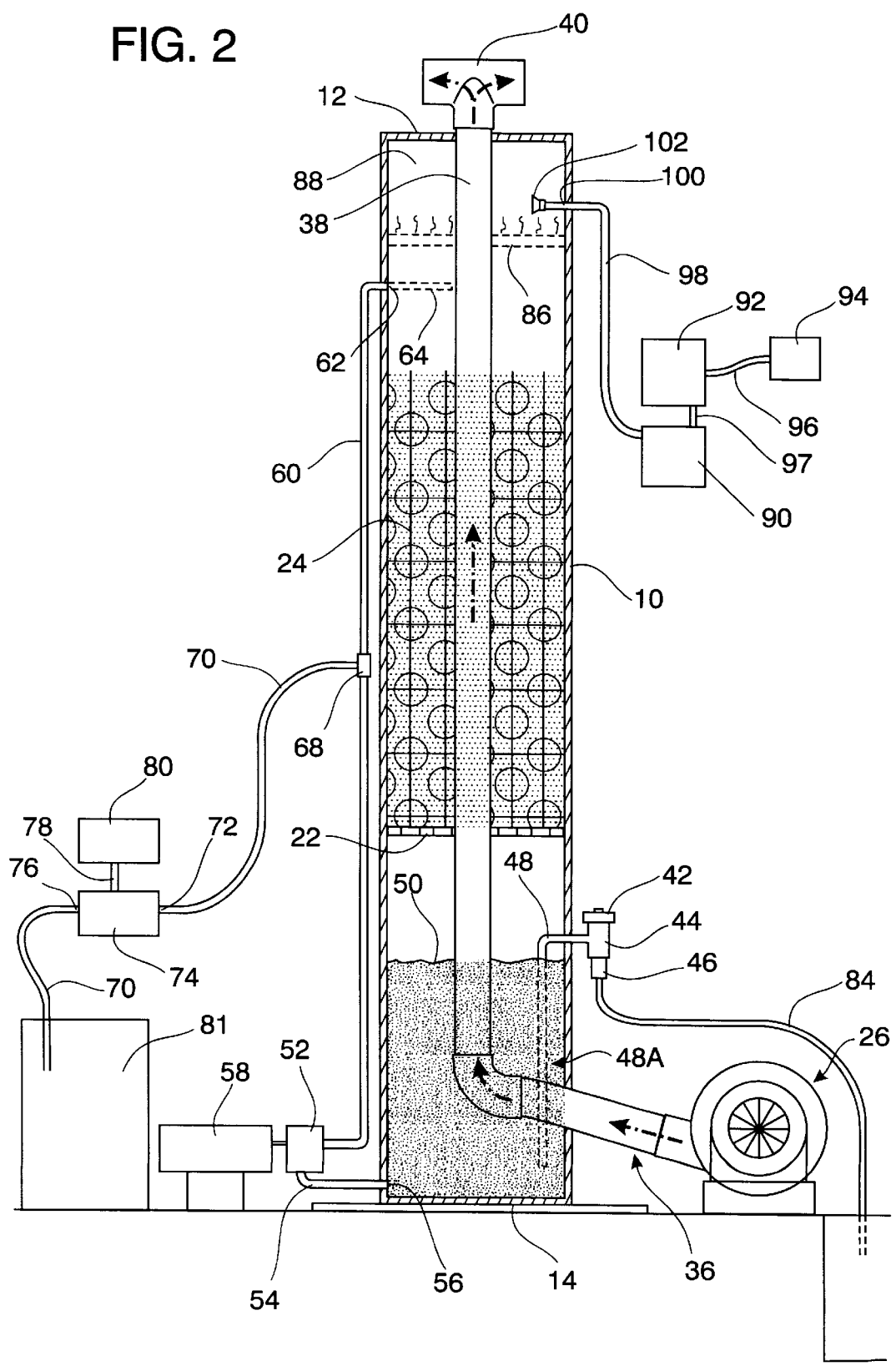
FIG. 2 is another cross-sectional elevational view essentially taken 90° from that of FIG. 1, the contact tower and associated equipment.
Figure 3:
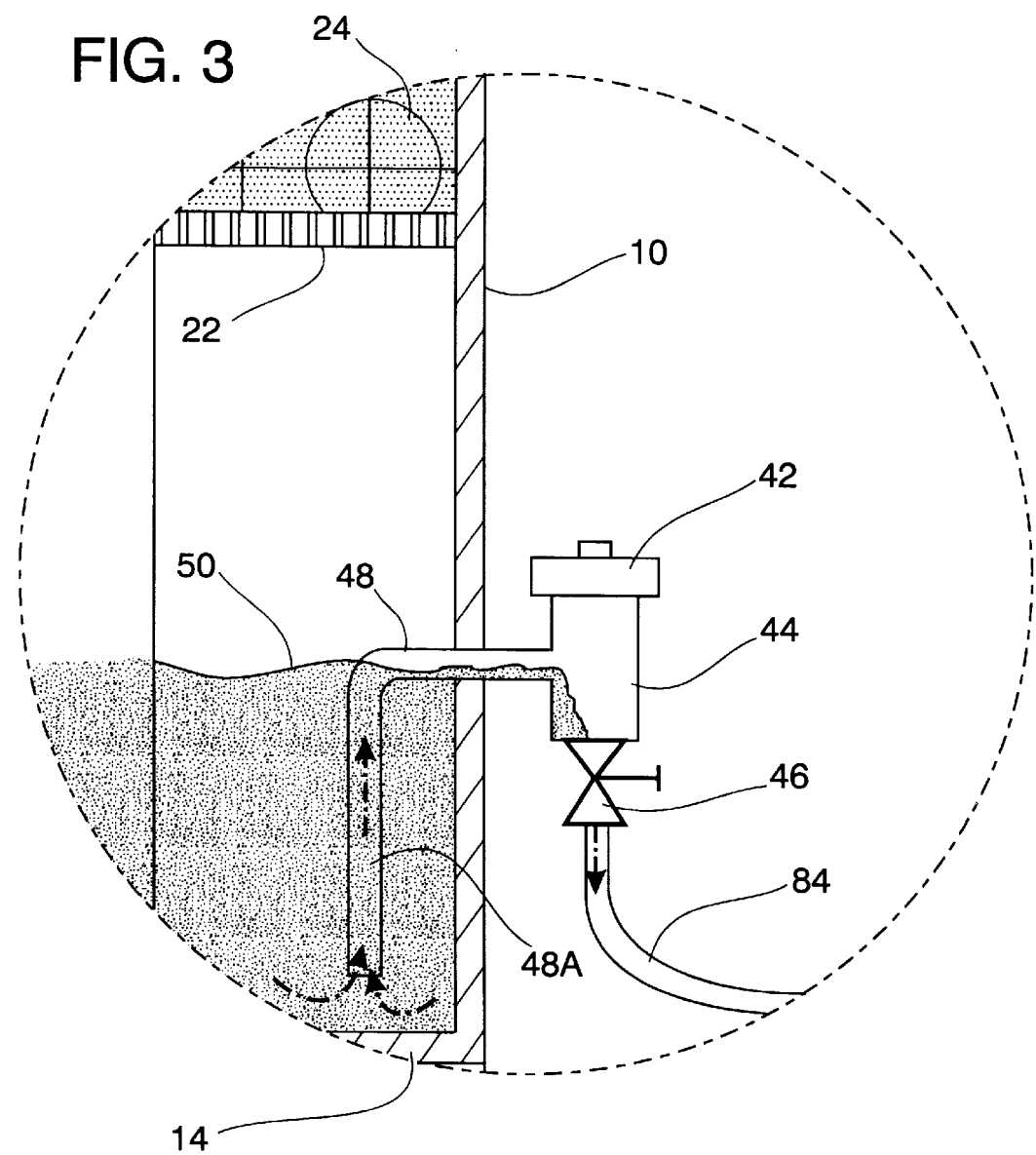
FIG. 3 is an enlarged elevational view of a segment of FIG. 2 showing more details of the system by which enzyme solution is introduced into the tower and excess solution withdrawn from the bottom of the tower.

In order to abate the odors of the sewer gas, this invention employs a unique combination of enzyme solution and ozone. When the system is first placed in operation a fill cap 42 (see FIGS. 2 and 3) is removed from a fill/overflow apparatus 44. A drain valve 46 below apparatus 44 is closed and with fill cap 42 removed, enzyme solution is added to flow through a pipe 48 extending through the wall of tower 10. Sufficient enzyme solution is added to reach a level 50 that is below support plate 22. After level 50 is reached, fill cap 42 is replaced and drain valve 46 is open. A vertical extension 48A of pipe 48 drains excess enzyme solution out of tower 10 from adjacent the tank bottom 14. Enzyme solution useful in the system of this invention is commercially available from Enzymatic Odor Solutions, Inc. a Florida corporation located at 1811 Bayberry Drive, Pembroke Pines, Fla. 33027 under the trademark, "AVAST 660+".

An enzyme circulating pump 52 has an inlet connected by pipe 54 to an opening 56 in tower 10, opening 56 being adjacent to and above tower bottom 14. Pump 52, powered by a motor 58, draws enzyme solution from the lower portion of the tower and conveys it, by vertical conduit 60 to inlet opening 62 in the upper portion of the tower. Within the interior of the tower, in the top portion thereof, a horizontal pipe 64 extending through opening 62 terminates in a spray nozzle 66. Enzyme solution is recirculated from the lower portion of the tower, through pump 52, vertical conduit 60, horizontal conduit 64 and spray nozzle 66 to be injected into the interior of the tower and to pass downwardly through packing 24. As the enzyme migrates downwardly it thoroughly contacts the surfaces of the packing, causing wetted surfaces that are contacted by the upwardly flowing sewer gas.

Enzyme solutions are commercially available and are typically obtained from natural fermentation of food grade materials by the use of multiple strains of bacteria to obtain a concentrated enzyme soup. This concentrated enzyme soup is employed in a mixture including micro-nutrients and biocatalyst to provide a solution that biodegrades odor produced as components of sewer gas. While commercially available odor abating enzyme solutions are available that can be used in the invention, proprietary enzyme solutions may also be used.

It is important that fresh enzyme solution be supplied to the system and for this purpose a venturi 68 is installed in conduit 60 through which the recirculated enzyme solution flows. Venturi 68 functions in a customary manner to derive from the flowing liquid stream a vacuum that is coupled by a conduit or hose 70 to the outlet 72 of a solenoid valve 74. Connected to the inlet 76 of the solenoid valve is a conduit 70 extending from a reservoir 81 which is kept supplied with fresh enzyme solution. Solenoid valve 74 is controlled between open and closed positions by a timer 80, the timer and solenoid valve being connected by a conductor 78. When valve 74 is open the vacuum obtained from venturi 68 is applied through conduit 70 to withdraw fresh enzyme solution from reservoir 81. The fresh enzyme solution is passed into the recirculated enzyme solution flowing through conduit 60. By regulating the open/closed time relationship supplied by timer 80, the quantity of fresh enzyme solution continually added to the recirculated enzyme solution can be controlled. Typically, timer 80 may close solenoid valve 74 for 240 seconds, then open the valve for 10 seconds, and constantly repeat this cycle. If more fresh enzyme solution is required the operator can adjust timer 80 to increase the percentage of time that solenoid valve 74 is open.

As enzyme accumulates within the lower portion of tower 10 it is automatically discharged through fill/overflow apparatus 44 and drain valve 46 to flow by a conduit or hose 84 for discharge, such as back into the sewer system.

Positioned within the upper portion of tower 10 is a demisting plate 86 that serves to extract any excess fluid, such as enzyme solution, from the upwardly passing gas before the gas is discharged through outlet opening 30. To further treat odor contaminants within the gas an ozone contact chamber 88 is maintained in the upper portion of the tower 10. Ozone gas is created by an ozone generator 90 located adjacent to the tower 10. Ambient air drawn in by compressor 94 passes through an air preparation unit 92. Compressed air from air compressor 94 passes through conduit 96 into and through the air preparation unit 92, then to the ozone generator 90 by conduit 97, then through conduit 98 through an opening 100 into an ozone dispensing nozzle 102 located within the tower then into the ozone contact chamber 88 located in tower 10 above the demisting plate 86 and within the ozone contact chamber 88.

Sewer gas passing upwardly in the tower through packing 24 contacts enzyme solution wherein biological reaction serves to neutralize malodorous components including hydrogen sulfide. Hydrogen sulfide and other non biological components of the sewer gas are further neutralized by ozone within ozone chamber 88. Sewer gases and ozone are thoroughly mixed as they pass downwardly through tower contact pipe 32. The enzyme solution is preferably formulated to be substantially neutral, that is having a pH of about 7 to 8 so, that it is neither substantially acidic or basic and therefore as acceptable for release to the atmosphere. The ozone helps to ensure that any living organisms that might be moved by the sewer gas are killed so that live bacteria is not discharged from the system to the atmosphere.

Tower 10 is a non-pressurized vessel. Under optimum operating conditions gas discharged from the system is non-toxic, noncorrosive, noncombustible and substantially odor free. To test for effectiveness of the system, measurements for gas odor should be taken one to two feet from exit 40.

As the solution passes downwardly through packing 24 it creates a liquid film. As this film builds up the biodegradation of odors of upwardly passing gases improves. Further the resultant film results in the creation of massive colonies of arobic bacteria that further enhances the effectiveness of the system.

The claims and the specification describe the invention presented and the terms that are employed in the claims draw their meaning from the use of such terms in the specification. The same terms employed in the prior art may be broader in meaning than specifically employed herein. Whenever there is a question between the broader definition of such terms used in the prior art and the more specific use of the terms herein, the more specific meaning is meant.

While the invention has been described with a certain degree of particularity, it is manifest that many changes may be made in the details of construction and the arrangement of components without departing from the spirit and scope of this disclosure. It is understood that the invention is not limited to the embodiments set forth herein for purposes of exemplification, but is to be limited only by the scope of the attached claim or claims, including the full range of equivalency to which each element thereof is entitled.

What is claimed:

1. A system for deodorizing malodorous sewer gas comprising:

a tower having a gas inlet and a vertically separated gas outlet, malodorous gas passing into the tower through the gas inlet;

an array of packing within said tower interposed between said tower inlet and tower outlet;

an enzyme solution circulation system that withdraws enzyme solution from an interior bottom portion of said tower and introduces the enzyme solution into an upper portion of said tower, the enzyme solution passing downward through said packing;

a blower for moving malodorous gas into said tower inlet and out said tower outlet, the malodorous gas passing upwardly through said packing and contacting said enzyme solution passing downward through said packing; and an enzyme solution replenishment system connected to said enzyme solution circulation system.

2. A system for deodorizing malodorous sewer gas according to claim 1 wherein said enzyme solution is in the form of a liquid medium having food grade material therein that has been fermented using multiple strains of bacteria.

3. A system for deodorizing malodorous sewer gas according to claim 2 wherein said liquid medium includes micro-nutrients and biocatalyst providing a solution that biodegrades odor producing components of sewer gas.

4. A system for deodorizing malodorous sewer gas according to claim 1 wherein said enzyme solution circulation system includes a venturi and wherein said enzyme solution replenishment system includes a reservoir of enzyme solution connected to said venturi.

5. A system for deodorizing malodorous sewer gas according to claim 4 wherein a timed control valve is interposed between said reservoir of enzyme solution and said venturi whereby the rate of replenishment of enzyme solution is controllable.

6. A system for deodorizing malodorous sewer gas according to claim 1 wherein said gas inlet is adjacent a bottom end of said tower and said gas outlet is adjacent a top end of said tower.

7. A system for deodorizing malodorous sewer gas according to claim 1 including a gas contact chamber in said tower through which enzyme treated gases pass after passing through said array of packing and including:

a source of ozone gas; and an ozone gas delivery system for delivering ozone gas into said gas contact chamber whereby enzyme treated gasses are mixed with ozone gas before passing out of said tower.

8. A system for deodorizing malodorous sewer gas according to claim 7 wherein said tower gas outlet communicates with said gas contact chamber and including:

a vertical tower contact pipe having an upper inlet end in communication with said tower gas outlet and a lower outlet end in communication with said blower, the tower contact pipe providing an environment for increased contact of enzyme treated gases with ozone gas from said gas contact chamber.

9. A system of deodorizing malodorous sewer gas according to claim 1 wherein said enzyme solution forms odor degrading film on said packing.

10. A method of deodorizing malodorous sewer gas comprising the steps of:

(1) flowing an enzyme solution downwardly within an upright tower while simultaneously passing malodorous sewer gas upwardly through the tower to provide enzyme treated sewer gas;

(2) mixing ozone gas with said enzyme treated sewer gas to provide a substantially odor free sewer gas; and (3) discharging the substantially odor free sewer gas to the environment.

11. A method of deodorizing malodorous sewer gas according to claim 10 wherein said upright tower of step (1) contains an array of packing through which said enzyme solution passes downwardly and said malodorous sewer gas passes upwardly.

12. A method of deodorizing malodorous sewer gas according to claim 10 including the step of recirculating said enzyme solution out from a lower portion and into an upper portion of said tower.

13. A method of deodorizing malodorous sewer gas according to claim 10 wherein said enzyme solution is in the form of a liquid medium having food grade material therein that has been fermented using multiple strains of bacteria.

* * * * *